(12) United States Patent
Guskey et al.

(10) Patent No.: US 6,183,730 B1
(45) Date of Patent: *Feb. 6, 2001

(54) ANTIPERSPIRANT AND DEODORANT COMPOSITIONS CONTAINING CYCLOHEXASILOXANE

(75) Inventors: Gerald John Guskey, Montgomery; Curtis Bobby Motley, West Chester, both of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/314,795

(22) Filed: May 18, 1999

(51) Int. Cl.[7] ............... A61K 7/32; A61K 7/34; A61K 7/38; A61K 7/00; A61K 31/74
(52) U.S. Cl. ............... 424/65; 424/66; 424/67; 424/68; 424/78.02; 424/400; 424/401
(58) Field of Search ............... 424/65, 66, 67, 424/68, 78.02, 400, 401

(56) References Cited

U.S. PATENT DOCUMENTS

| | | | |
|---|---|---|---|
| 4,126,679 | 11/1978 | Davy et al. | 424/66 |
| 4,673,570 | 6/1987 | Soldati | 424/66 |
| 5,417,964 | 5/1995 | Carlson, Sr. et al. | 424/66 |
| 5,449,511 | 9/1995 | Coe | 424/66 |
| 5,531,986 | 7/1996 | Shevade et al. | 424/68 |
| 5,922,309 | 7/1999 | Brewster | 424/65 |

FOREIGN PATENT DOCUMENTS

| | | |
|---|---|---|
| 61-155318 | 7/1986 | (JP) . |
| WO 91/04009 | 4/1991 | (WO) . |
| WO 95/24887 | 9/1995 | (WO) . |
| WO 97/36572 | 10/1997 | (WO) . |
| WO 98/32418 | 7/1998 | (WO) . |

*Primary Examiner*—Shelley A. Dodson
(74) *Attorney, Agent, or Firm*—William J. Winter

(57) ABSTRACT

Disclosed are antiperspirant and deodorant compositions having improved stability, low residue performance and/or improved cosmetics. These compositions comprise select concentrations of cyclohexasiloxane as a volatile silicone material from about 0.1% to about 50% by weight of an antiperspirant active, and from about 0.1% to about 50% by weight of a suspending agent, wherein the compositions are preferably substantially free of cyclotetrasiloxane. The selection of cyclohexasiloxane over other volatile silicone materials provides improved low residue performance, and especially when formulated as an aqueous emulsion it provides improved product stability in the form of extended duration of time within which the emulsion remains clear or nearly so.

33 Claims, No Drawings

ANTIPERSPIRANT AND DEODORANT COMPOSITIONS CONTAINING CYCLOHEXASILOXANE

TECHNICAL FIELD

The present invention relates to antiperspirant and deodorant compositions comprising cyclohexasiloxane as a volatile silicone carrier for improved product stability, performance and/or cosmetics.

BACKGROUND OF THE INVENTION

There are many types of topical antiperspirant and deodorant products that are commercially available or otherwise known in the antiperspirant and deodorant art. Most of these products are formulated as aerosol or pump sprays, roll-on liquids, creams, emulsions, gels, gel-solids, or other solid or semi-solid stick formulations, and comprise a deodorant (e.g., triclosan) and/or astringent material (e.g. zirconium and/or aluminum salts) incorporated into a suitable carrier. These products are designed to provide effective perspiration and/or odor control while also being cosmetically acceptable during and after application onto the axillary area or other areas of the skin.

Within this product group, antiperspirant and deodorant products containing volatile silicone fluids have become especially popular among consumers. These products can be aqueous or anhydrous and contain up to about 90% by weight of a volatile silicone fluid, most typically cyclotetrasiloxane and/or cyclopentasiloxane. The volatile silicone provides the composition with dry skin feel during application, and because of its volatility, evaporates quickly after application leaving the applied surface feeling smooth and dry with no residual white marks resulting from the volatile silicone material.

There are, however, a number of limitations associated with the use of these volatile silicone materials in antiperspirant formulations. These materials quickly evaporate from the skin after application leaving behind a residue of other solid materials such as antiperspirant active and suspending agent on the skin. Because of this residue problem, these volatile silicones are typically used in combination with residue masking materials such as liquid dimethicones and other non-volatile silicone and organic emollients. It has also been found that antiperspirant clear emulsions containing volatile silicone are less stable and result in whitening of the clear emulsion over time.

It has now been found that antiperspirant and deodorant compositions containing volatile silicones can provide improved low residue performance and/or product stability by selecting as the volatile silicone material, cyclohexasiloxane. These selected volatile silicones provide antiperspirant compositions with reduced visible residue after topical application, and when formulated into a clear emulsion, provides improved product stability in the form of reduced whitening or cloud formation over time within the formulated emulsion.

It is therefore an object of the present invention to provide a low-residue antiperspirant and deodorant composition containing cyclohexasiloxane as the selected volatile silicone material, and further to provide a clear antiperspirant emulsion having improved stability and which contains cyclohexasiloxane. It is yet a further object of the present invention to provide such a clear antiperspirant emulsion that maintains product clarity over longer periods of time as compared to similar other compositions containing other volatile silicone materials.

SUMMARY OF THE INVENTION

Disclosed are antiperspirant and deodorant compositions having improved product stability and/or low residue performance. These compositions comprise cyclohexasiloxane at select concentrations, antiperspirant active, and suspending agent, wherein the compositions are preferably substantially free of cyclotetrasiloxane.

It has been found that the selection of cyclohexasiloxane over other volatile silicone materials such as cyclotetrasiloxane and cyclopentasiloxane provides improved low residue performance, and especially when formulated as an aqueous emulsion provides improved product stability in the form of extended duration of time within which the emulsion remains clear or translucent.

DETAILED DESCRIPTION OF THE INVENTION

The antiperspirant and deodorant compositions of the present invention comprise as essential ingredients an antiperspirant active, a suspending agent, and a volatile silicone material containing cyclohexasiloxane.

The term "volatile" as used herein, unless otherwise specified, refers to those materials that are liquid under ambient conditions and have a vapor pressure as measured at 25° C. of at least about 0.01 mmHg, typically from about 0.01 mmHg to about 6.0 mmHg, Conversely, the term "nonvolatile" as used herein, unless otherwise specified, refers to those materials which are not volatile as that term is defined herein. Such "nonvolatile" materials will typically be in the form of a liquid, semi-solid or solid, and have no measurable vapor pressure as measured at 25° C.

The term "anhydrous" as used herein refers to those antiperspirant and deodorant embodiments of the present invention that are substantially free of added water. From a formulation standpoint, this means that such embodiments contain less than about 5%, more preferably less than about 3%, even more preferably less than about 1%, most preferably zero percent, by weight of free or added water, other than the water of hydration typically associated with particulate antiperspirant active.

The term "ambient conditions" as used herein refers to surrounding conditions at about one atmosphere of pressure (1 atm), at about 50% relative humidity, and at about 25° C., unless otherwise specified. All values, amounts and measurements described herein are obtained under ambient conditions unless otherwise specified.

The term "substantially free" as used herein to characterize cyclotetrasiloxane concentrations in the compositions of the present invention means that these compositions preferably contain less than about 1% by weight of cyclotetrasiloxane, more preferably zero percent by weight of cyclotetrasiloxane.

The antiperspirant and deodorant compositions of the present invention, including corresponding methods of the present invention, can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

The essential elements of the compositions and methods of the present invention are described in greater detail hereinafter.

I. Antiperspirant Active

The antiperspirant and deodorant compositions of the present invention comprise an antiperspirant active suitable for application to human skin. The antiperspirant active in the composition may be solubilized or in the form of solid particulates. The concentration of antiperspirant active in the composition should be sufficient to provide the desired perspiration wetness and/or odor control.

The antiperspirant and deodorant compositions of the present invention preferably comprise antiperspirant active at concentrations ranging from about 0.1% to about 50%, more preferably from about 5% to about 35%, even more preferably from about 7% to about 20% by weight of the composition. These weight percentages are calculated on an anhydrous metal salt basis exclusive of water and any complexing agents such as glycine, glycine salts, or other complexing agents. The antiperspirant active may be solubilized, partially solubilized, or in the form of particulate solids. These compositions may also be aqueous or anhydrous. The active may be solubilized or partially solubilized in the antiperspirant composition with the help of additional solvents or co-solvents which are known or otherwise effective for solubilizing antiperspirant active, and which are compatible with the selected components of the antiperspirant composition or which otherwise do not unduly impair product performance.

The antiperspirant active for use in the compositions of the present invention include any compound, composition or other material having antiperspirant activity. Preferred antiperspirant actives include astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant compositions include those which conform to the formula:

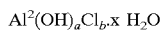

$$Al^2(OH)_aCl_b \cdot x \; H_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975: U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant and deodorant compositions include those which conform to the formula:

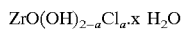

$$ZrO(OH)_{2-a}Cl_a \cdot x \; H_2O$$

wherein a is from about 1.1 to about 2.0; x is from about 1 to about 8; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

II. Deodorant Active

The compositions of the present invention can also be formulated with deodorant active in addition to or in place of the antiperspirant active described hereinbefore. These compositions may contain a deodorant active, perfume or combination thereof. Concentrations of the deodorant active range from about 0.1% to about 10%, preferably from about 0.1% to about 5%, more preferably from about 0.1% to about 1%, even more preferably from about 0.1% to about 0.5%, by weight of the deodorant composition. These deodorant actives and perfumes include any known or otherwise safe and effective deodorant active or perfume suitable for topical application to human skin.

Deodorant actives suitable for use herein include any topical material that is known for or otherwise effective in preventing or eliminating malodor associated with perspiration. These deodorant actives are typically antimicrobial agents (e.g., bacteriocides, fungicides), malodor-absorbing materials, or combinations thereof.

Preferred deodorant actives are antimicrobial agents, non-limiting examples of which include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-inyristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, phenoxyethanol, and combinations thereof. Most preferred are triclosan and triclocarban.

Perfumes suitable for use in the compositions of the present invention include any topical material that is known for or otherwise effective in masking malodor associated with perspiration, or which otherwise provides the composition with the desired perfumed aroma. These include any perfume or perfume chemical, including pro-perfumes and deo-perfumes, suitable for topical application to the skin.

III. Cyclohexasiloxane

The antiperspirant and deodorant compositions of the present invention comprise cyclohexasiloxane. It has been found that selection of cyclohexasiloxane in addition to or in place of other volatile silicone materials such as cyclopentasiloxane and/or cyclotetrasiloxane provides the composition with improved product stability, low residue performance, and/or improved cosmetics.

The antiperspirant and deodorant compositions of the present invention comprise cyclohexasiloxane as a volatile carrier liquid. Concentrations range from about 1% to about 99.8%, preferably from about 10% to about 99.8%, even more preferably from about 30% to about 99.8%, most preferably from about 30% to about 75%, by weight of the composition.

The compositions may further comprise other volatile silicone liquids in addition to cyclohexasiloxane described herein. For those embodiments of the present invention comprising other additional volatile silicone liquids, the cyclohexasiloxane preferably represents from about 10% to about 99% by weight of the total volatile silicone concentration, more preferably from about 30% to about 99%, even more preferably from about 45% to about 99%, most preferably from about 95% to about 99%.

The antiperspirant and deodorant compositions of the present invention may therefore comprise volatile silicone materials other than and in addition to the cyclohexasiloxane. These other volatile silicone materials may be cyclic, linear or branched chain silicones, but are preferably substantially free of cyclotetrasiloxane. In this context, the phrase "substantially free" means that the antiperspirant and deodorant compositions of the present invention preferably contain less than about 5%, preferably less than about 1%, most preferably zero percent, by weight of cyclotetrasiloxane. It has been found that that cyclohexasiloxane provides the compositions with improved stability, low-residue application, and/or improved cosmetics as compared to other more volatile silicone materials, especially as compared to cyclotetrasiloxane. Nonlimiting examples of suitable volatile silicone materials are described in Todd et al., "Volatile Silicone Fluids for Cosmetics", Cosmetics and Toiletries, 91:27–32 (1976), which descriptions are incorporated herein by reference.

The other optional volatile silicone materials are preferably cyclic, and may have from 3 to 5 and/or from 7 to 10 silicon atoms, more preferably either 5 or 7 silicon atoms, most preferably 5 silicon atoms (cyclopentasiloxane). These volatile cyclic silicone materials as optional ingredients, and cyclohexasiloxane as an essential ingredient, conform to the formula:

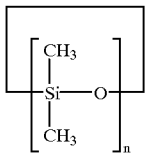

wherein n is from 3 to about 10, and n is 6 for cyclohexasiloxane (essential ingredient) and n is 5 for cyclopentasiloxane (preferred optional carrier) or n is 7 for cycloheptasiloxane (other optional carrier) and so forth. Optional volatile silicone materials for use herein include, but are not limited to, cyclopenitasiloxane (commercially available from G. E. Silicones); Dow Corning 245, 246 and 344 (available from Dow Coming Corp.); GE 7207, GE 7158 and Silicone Fluid SF-1202 (available from General Electric Co.); ABIL B8839 (available from Goldschmidt); KF995 (available from Shin-Etsu) and combinations thereof Nonlimiting examples of cyclohexasiloxane materials, and materials containing cyclohexasiloxane and other volatile silicones, suitable for use in the composition include Dow Corning 246 and 345 (available from Dow Corning Corp.).

The composition of the present invention may further comprise from about 1% to about 65%, preferably from about 5% to about 40%, by weight of other optional liquid carriers in addition to or in place of the other optional volatile silicone materials described herein, the selection of which may depend upon factors such as the formulation and ingredients selected, and the product performance desired. These other optional carriers may be polar or non-polar, volatile or nonvolatile, organic or inorganic carriers, and include those carrier liquids that are known for use in antiperspirant and deodorant or other personal care products, or which are otherwise safe and effective for topical application to human skin. Examples of such other optional liquid carriers include those described in U.S. Pat. No. 5,750,096 (Guskey); U.S. Pat. No. 5,733,534 (Sawin et al.); U.S. Pat. No. 5,718,890 (Putman et al.); U.S. Pat. No. 5,429,816 (Hofrichter et al.); U.S. Pat. No. 5,605,681 (Trandai et al.); and U.S. Pat. No. 5,585,092 (Trandai et al.), which descriptions are incorporated herein by reference.

The antiperspirant and deodorant compositions of the present invention preferably further comprise a nonvolatile silicone material as an optional ingredient, more preferably a polydimethylsiloxane fluid, at concentrations ranging from about 1% to about 35%, even more preferably from about 2% to about 20%, by weight of the composition. Preferred are those compositions containing a combination of volatile and nonvolatile silicones such as those described in U.S. Pat. No. 5,156,834 (Beckmeyer et al.), which patent is incorporated herein by reference. These combinations of volatile and nonvolatile silicones may be formulated into the compositions of the present invention in the manner suggested by the Beckmeyer et al. patent, wherein the formulations may take on any product form, e.g., solid, liquid, semi-solid.

IV. Suspending or Thickening Agent

The antiperspirant and deodorant compositions of the present invention may further comprise a suspending or thickening agent to help provide the composition with the desired viscosity, rheology, texture or product hardness, or to otherwise help suspend any dispersed solids or liquids within the composition. The terms "suspending agent" and "thickening agent" are used interchangeably herein and include any material known or otherwise effective in providing suspending, gelling, viscosifying, solidifying or thickening properties to the composition or which otherwise provide structure to the final product form. These suspending or thickening agents include gelling agents, and polymeric or nonpolymeric or inorganic thickening or viscosifying agents. Such materials will most typically be solids under ambient conditions and include organic solids, silicone solids, crystalline or other gellants, inorganic particulates such as clays or silicas, or combinations thereof.

The concentration and type of suspending or thickening agent selected for use in the antiperspirant composition will vary depending upon the desired product form, viscosity, hardness and/or other product characteristics. For most suspending or thickening agents suitable for optional use herein, the concentration will most typically range from about 0.1% to about 50%, more typically from about 1% to about 35%, preferably from about 1% to about 25%, most preferably from about 1% to about 15%, by weight of the composition.

Suitable suspending or thickening agents in the antiperspirant and deodorant compositions include, but are not limited to, fatty acid gellants, salts of fatty acids, hydroxy acid gellants, esters and amides of fatty acid or hydroxy fatty acid gellants, cholesterolic materials, dibenzylidene alditols, lanolinolic materials, fatty alcohols, triglycerides, sucrose esters, inorganic materials such as clays or silicas, and other suitable gellants.

Other suitable suspending or thickening agents include gellants such as fatty alcohols having from about 8 to about 40 carbon atoms, preferably from 8 to about 30 carbon atoms, more preferably from about 12 to about 18 carbon atoms. These gellants are wax-like materials which are most typically used at concentrations ranging from about 1% to about 30%, preferably from about 5% to about 20%, most preferably from about 10% to about 20%, by weight of the antiperspirant and deodorant compositions. Preferred are cetyl alcohol, myristyl alcohol, stearyl alcohol, behenyl alcohol, and combinations thereof, more preferably stearyl alcohol.

Other suitable suspending or thickening agents include waxes or wax-like materials having a melt point of above 65° C., more typically from about 65° C. to about 130° C., examples of which include, but are not limited to, waxes such as beeswax, carnauba, baysberry, candelilla, montan, ozokerite, ceresin, hydrogenated castor oil (castor wax), synthetic waxes, microcrystalline waxes. Castor wax is preferred within this group. Other high melting point waxes are described in U.S. Pat. No. 4,049,792 (Elsnau), which description is incorporated herein by reference.

Other suitable suspending or thickening agents include fatty acid gellants such as fatty acid and hydroxy acids such as alpha or beta hydroxy fatty acids, having from about 10 to about 40 carbon atoms, and esters and amides of such gelling agents. Nonlimiting examples such gellants include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred are 12-hydroxystearic acid, esters of 12-hydroxystearic acid, amides of 12-hydroxystearic acid and combinations thereof, and all other gelling agents which correspond to the following formula:

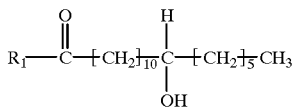

wherein $R_1$ is $OR_2$, $NR_2R_3$, or a silicone containing moiety; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof; even more preferably, 12-hydroxystearic acid, isopropyl amide of 12-hydroxystearic acid, and combinations thereof. Most preferred is 12-hydroxystearic acid.

Suitable amide gellants include disubstituted or branched monoamide gellants, monosubstituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816 (Hofrichter et al.) and U.S. Pat. No. 5,840,287 (Guskey et al.), which descriptions are incorporated herein by reference. Concentrations of all such gellants preferably range from about 0.1% to about 25%, more preferably of from about 1% to about 15%, more preferably from about 1% to about 10%, by weight of the antiperspirant and deodorant compositions.

Other suitable suspending or thickening agents include triglyceride gellant systems which comprise glyceryl tribehenate and other triglycerides, wherein at least about 75%, preferably about 100%, of the esterified fatty acid moieties of said other triglycerides each have from about 18 to about 36 carbon atoms, and wherein the molar ratio of glyceryl tribehenate to said other triglycerides is from about 20:1 to about 1:1, preferably from about 10:1 to about 3:1, more preferably from about 6:1 to about 4:1. The esterified fatty acid moieties may be saturated or unsaturated, substituted or unsubstituted, linear or branched, but are preferably linear, saturated, unsubstituted ester moieties derived from fatty acid materials having from about 18 to about 36 carbon atoms. The triglyceride gellant material preferably has a melting point of at less than about 110° C., preferably between about 50° C. and 110° C.

Nonlimiting examples of some commercially available triglyceride gellants for use in the compositions include tristearin, tribehenin, C18–36 triglycerides, hydrogenated vegetable oil, trihydroxysterin (Thixcin® R, available from Rheox, Inc.), rape seed oil, castor wax, fish oils, tripalmitin, and linear Syncrowaxes® such as Syncrowax® HRC and Syncrowax® HGL-C (Syncrowax® available from Croda, Inc.).

Other suitable suspending or thickening agents for use in the antiperspirant and deodorant compositions include particulate suspending or thickening agents such as clays and colloidal pyrogenic silica pigments. Other known or otherwise effective particulate suspending or thickening agents can likewise be used in the antiperspirant composition. Concentrations of optional particulate thickening agents preferably range from about 0.1% to about 15%, more preferably from about 1% to about 15%, even more preferably from about 1% to about 8%, by weight of the composition. Colloidal pyrogenic silica pigments are preferred, a common example of which includes Cab-O-Sil®, a submicron particulated pyrogenic silica.

Suitable clay suspending or thickening agents include montmorillonite clays, examples of which include bentonites, hectorites, and colloidal magnesium aluminum silicates. These and other suitable clay suspending agents are preferably hydrophobically treated, and when so treated will generally be used in combination with a clay activator. Nonlimiting examples of suitable clay activators include propylene carbonate, ethanol, and combinations thereof. The amount of clay activator will typically range from about 25% to about 75% by weight of the clay, more typically from about 40% to about 60% by weight of the clay.

Preferred thickening or gelling agents for the deodorant embodiments of the present invention are the salts of fatty acids, wherein the fatty acid moiety has from about 12 to about 40 carbon atoms, preferably from about 12 to about 22 carbon atoms, more preferably from about 16 to about 20 carbon atoms, most preferably about 18 carbon atoms. Suitable salt forming cations for use with these gelling agents include metal salts such as alkali metals, e.g. sodium and potassium, and alkaline earth metals, e.g. magnesium, and aluminum. Preferred are sodium and potassium salts, more preferably sodium stearate, sodium palmitate, potassium stearate, potassium palmitate, sodium myristate, aluminum monostearate, and combinations thereof. Most preferred is sodium stearate.

V. Other Optional Materials

The antiperspirant and deodorant compositions of the present invention may further comprise one or more other optional materials that are known for use in antiperspirant and deodorant compositions or other personal care products, or which are otherwise suitable for topical application to human skin.

Nonlimiting examples of such other optional materials include dyes or colorants, emulsifiers, perfumes, distributing agents, pharmaceutical or other topical active, preservatives, surfactants, processing aides such as viscosity modifiers, wash-off aids, and so forth. Examples of such optional materials are described in U.S. Pat. No. 4,049,792 (Elsnau); U.S. Pat. No. 5,019,375 (Ianner et al.); and U.S. Pat. No. 5,429,816 (Hofrichter et al.); which descriptions are incorporated herein by reference.

VI. Product Form

The antiperspirant and deodorant compositions of the present invention can be formulated as any known or otherwise effective product from suitable for providing topical application of antiperspirant and deodorant active to the desired area of the skin. Nonlimiting examples of such product forms include liquids such as aerosols, nonaerosol sprays and roll-ons; solids such as gel solids, solid sticks, and suspensoids; semi-solids/liquids such as soft solids, creams and lotions; and so forth.

VII. Specific Embodiments

The antiperspirant and deodorant embodiments of the present invention all comprise an antiperspirant and/or deodorant active, a suspending or thickening agent, and cyclohexasiloxane. Nonlimiting examples of these specific embodiments are described below.

The compositions of the present invention include antiperspirant and deodorant embodiments comprising a) from about 30% to about 99.8%, preferably from about 40% to about 70%, by weight of cyclohexasiloxane; b) from about 0.1% to about 50% by weight of an antiperspirant active; and c) from about 0.1% to about 50% by weight of a suspending agent, wherein the compositions are substantially free of cyclotetrasiloxane.

Another embodiment of the present invention is directed to anhydrous antiperspirant and deodorant compositions comprising a) from about 20% to about 99.8%, preferably from about 30% to about 70%, by weight of cyclohexasiloxane; b) from about 0.1% to about 50% by weight of an antiperspirant active; and c) from about 0.1 % to about 50% by weight of a suspending agent, wherein the compositions are substantially free of cylclotetrasiloxane and water.

Yet another embodiment of the present invention is directed to antiperspirant and deodorant compositions comprising a) from about 1% to about 99% by weight of cyclohexasiloxane, b) from about 0.1% to about 50% by weight of an antiperspirant active selected from the group consisting of zirconium salts, aluminum salts, and combinations thereof; and c) from about 0.1% to about 50% by weight of a gellant selected from the group consisting of 12-hydroxysteric acid, 12-hydroxystearic acid esters, 12-hydroxystearic acid amides, n-acyl amino acid amides, n-acyl amino acid esters, triglyceride gellants (e.g., Synchrowax HRC and/or Synchrowax HGL-C), sucrose ester fatty acids, and combinations thereof.

The compositions of the present invention also include deodorant embodiments comprising a) from about 5% to about 99% by weight of cyclohexasiloxane, b) from about 0.1% to about 10% by weight of deodorant active, and c) from about 0.1% to about 50% by weight of a suspending agent, wherein the compositions are substantially free of nitrogen-containing polymers and cyclotetrasiloxane, and wherein the compositions are only in the form of liquids or semi-solids/liquids.

Clear Gel Emulsions

The compositions of the present invention also include those embodiments formulated as clear gel emulsions. These emulsions are aqueous compositions having a clear or translucent appearance, and which comprise a) from about 5% to about 50%, preferably from about 10% to about 40%, by weight of cyclohexasiloxane, b) from about 0.1% to about 35%, preferably from about 5% to about 35% by weight of solubilized antiperspirant active, c) from about 1% to about 35%, preferably from about 1% to about 25%, by weight of a gelling agent, d) from about 1% to about 70%, preferably from about 10% to about 50%, by weight of water, and e) from about 5% to about 25%, preferably from about 10% to about 20%, by weight of an emulsifying agent.

It has been found that the use of cyclohexasiloxane in the clear gel emulsions described herein are especially effective in maintaining product clarity for extended periods of time. It has been found that similar emulsions containing the more volatile silicone liquids such as cyclopentasiloxane and cyclotetrasiloxane rather than cyclohexasiloxane more readily develop a milky or cloudy appearance over time.

Gelling agents for use in the aqueous gel emulsions include any of the gelling agents described herein, preferably the dimethicone copolyol and/or cyclomethicone-dimethicone copolyol gelling agents.

The emulsifying agent for use in the clear aqueous gel embodiments may be any emulsifying agent suitable for helping maintain the stability of the emulsion, which will typically be a two phase water-ill-silicone or silicone-in-water emulsion. Preferred are emulsifying agents are cyclomethicone-dimethicone copolyol fluids having a viscosity at 25° C. of 600–2,000 centipoise (cps), a specific gravity at 25° C. of about 0.963, a nonlimiting example of which includes Dow Corning 3225C.

Specific examples of the formulation embodiments described hereinbefore are set forth hereinafter in Tables 1–5 as Examples 1–26.

VIII. Methods of Manufacture

The antiperspirant and deodorant compositions of the present invention may be prepared by any known or otherwise effective technique, suitable for providing an antiperspirant and deodorant composition of the desired form and having the essential materials described herein. Many such techniques are described in the antiperspirant/deodorant and formulation arts for each of the described product forms.

IX. Method of Use

The antiperspirant and deodorant compositions may be applied topically to the axilla or other area of the skin in an amount effective to treat or reduce perspiration wetness and/or malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied to the axilla or other area of the skin, one or two times daily, preferably once daily, to achieve effective antiperspirant and/or malodor control over an extended period.

X. EXAMPLES

The following nonlimiting examples illustrate specific antiperspirant and deodorant embodiments of the present invention. Each of the exemplified compositions are prepared by methods well known in the formulation arts for preparing the various antiperspirant and deodorant product forms. All exemplified amounts are weight percents based on the total weight of the antiperspirant and deodorant compositions, unless otherwise specified.

EXAMPLES 1–7

The compositions described in Table 1 are antiperspirant compositions in the form of aqueous emulsions. These exemplified compositions can be prepared by methods well known in the art for aqueous emulsions, some examples of which are described in U.S. Pat. No. 4,673,570 (Soldati), which description is incorporated herein by reference.

TABLE 1

Antiperspirant and Deodorant Aqueous Emulsions

| Ingredient | Example 1 | Example 2 | Example 3 | Example 4 | Example 5 | Example 6 | Example 7 |
|---|---|---|---|---|---|---|---|
| Al Zr trichlorohydrex glycinate | 20.0 | 20.0 | 20.0 | 20.0 | 20.0 | 15.0 | — |
| Cyclohexasiloxane | 10.0 | 10.0 | 5.0 | 11.0 | 10.0 | 10.0 | 20.0 |
| Cyclopentasiloxane | — | — | 5.0 | — | — | 5.0 | — |
| Cyclomethicone (and) dimethicone copolyol DC 3225C | 15.0 | — | 15.0 | 12.0 | 15.0 | 12.0 | 20.0 |
| PPG-15 stearyl ether | 9.0 | — | — | — | 3.0 | 3.0 | — |
| Perfume | 1.0 | 1.0 | 1.0 | 1.0 | 1.0 | 1.0 | 2.7 |
| Water | 45.0 | 45.0 | 45.0 | 46.0 | 42.0 | 40.0 | 44.0 |
| Cyclopentasiloxane (and) dimethicone copolyol | — | 15 | — | — | — | — | — |
| Isopropyl myristate | — | 9.0 | — | — | — | — | — |
| PEG-8 | — | — | 9.0 | — | — | — | — |
| Dimethicone 50 cs | — | — | — | — | 4.0 | 4.0 | 1.0 |
| Ethanol | — | — | — | 5.0 | — | 5.0 | 6.0 |
| Propylene glycol | — | — | — | 5.0 | 5.0 | 5.0 | 6.0 |
| Triclosan | — | — | — | — | — | — | 0.3% |

EXAMPLES 8–12

The compositions described in Table 2 are antiperspirant and deodorant compositions in the form of solid sticks. These exemplified compositions can be prepared by methods well known in the art for preparing such product forms, examples of such methods including those described in U.S. Pat. No. 4,985,238 (Tanner et al.), which descriptions are incorporated herein by reference.

TABLE 2

Solid Antiperspirant Sticks

| Ingredient | Example 8 | Example 9 | Example 10 | Example 11 | Example 12 |
|---|---|---|---|---|---|
| Al Zr trichlorohydrex glycinate | 20.0 | 20.0 | 20.0 | 20.0 | 20.0 |
| Stearyl alcohol | 12.0 | 12.0 | 11.0 | 13.0 | 12.0 |
| Cyclohexasiloxane | 25.0 | 50.0 | 40.0 | 10.0 | 24.0 |
| Cyclopentasiloxane | 25.0 | — | 10.0 | 40.0 | 24.0 |
| Talc | 10.0 | 10.0 | 10.0 | 9.0 | 10.0 |
| Dimethicone 50 cs | 3.0 | 3.0 | 3.0 | 3.0 | 4.0 |
| Hydrogenated castor oil | 3.0 | 3.0 | 3.0 | 3.0 | 3.0 |
| Perfume | 1.0 | 1.0 | 2.0 | 1.0 | 2.0 |
| Silica | 0.4 | 0.4 | 0.4 | 0.4 | 0.4 |
| Microthene | 0.4 | 0.4 | 0.4 | 0.4 | 0.4 |
| Behenyl alcohol | 0.2 | 0.2 | 0.2 | 0.2 | 0.2 |

EXAMPLES 13–18

The antiperspirant and deodorant compositions described in Table 3 are formulated as aerosols and roll-on liquids. Each of these exemplified compositions can be prepared by methods well known in the art for preparing such product forms, examples of such methods including those described in U.S. Pat. No. 4,904,463 (Johnson et al.) and U.S. Pat. No. 5,298,236 (Orr et al.), which descriptions are incorporated herein by reference.

TABLE 3

Liquid Antiperspirant Roll-ons and Aerosols

| Ingredient | Example 13 (roll-on) | Example 14 (roll-on) | Example 15 (roll-on) | Example 16 (aerosol) | Example 17 (aerosol) | Example 18 (aerosol) |
|---|---|---|---|---|---|---|
| Cyclohexasiloxane | 43.3 | 23.3 | 23.0 | 16.4 | 10.0 | 8.0 |
| Cyclopentasiloxane | — | 20.0 | 10.0 | — | 8.0 | 11.0 |
| Dimethiconol 80 cs | 10.00 | — | — | — | — | — |
| Dimethicone 50 cs | — | 20.0 | 10.0 | 5.0 | 3.0 | 2.0 |
| Mineral oil | 10.0 | — | 20.0 | — | — | — |
| Al Zr trichlorohydrex gly. | 25.0 | 25.0 | 25.0 | — | — | — |
| Quaternium-18 Hectorite HL | 4.0 | 4.0 | 4.0 | 1.0 | 1.0 | 1.0 |
| Propylene carbonate | 1.0 | 1.0 | 1.0 | 0.3 | 0.3 | 0.3 |

TABLE 3-continued

Liquid Antiperspirant Roll-ons and Aerosols

| Ingredient | Example 13 (roll-on) | Example 14 (roll-on) | Example 15 (roll-on) | Example 16 (aerosol) | Example 17 (aerosol) | Example 18 (aerosol) |
|---|---|---|---|---|---|---|
| Dipropylene glycol | 0.9 | 0.9 | 0.9 | — | — | — |
| Polyethylene powder | 5.5 | 5.5 | 5.5 | — | — | — |
| Al chlorohydrate | — | — | — | 12.0 | 12.0 | 12.0 |
| Propellant | — | — | — | 60.0 | 60.0 | 60.0 |
| Isopropyl myristate | — | — | — | 5.0 | 5.0 | 5.0 |
| Perfume | 0.3 | 0.3 | 0.6 | 0.3 | 0.7 | 0.7 |

EXAMPLES 19–23

The compositions described in Table 4 are antiperspirant compositions in the form of gel solid sticks. Each of these exemplified compositions described are prepared by methods well known in the art for preparing such product forms, examples of such methods including those described in U.S. Pat. No. 5,429,816 (Hofrichter et al.), which descriptions are incorporated herein by reference.

TABLE 4

Gel Solid Antiperspirant Sticks

| Ingredient | Example 19 | Example 20 | Example 21 | Example 22 | Example 23 |
|---|---|---|---|---|---|
| Cyclohexasiloxane | 46.3 | 23.3 | 11.8 | 37.3 | 20.0 |
| Cyclopentasiloxane | — | 23.0 | — | 10.0 | 13.3 |
| Dimethiconol 80 cs | — | — | 26.0 | — | 10.0 |
| 12-Hydroxystearic Acid | 7 | 7 | 7 | 7 | 7 |
| N-Lauryl-Glutamic acid-di-n-butyl amide | 2 | 2 | 2 | 2 | 2 |
| Dipropylene Glycol | — | — | — | — | 0.5 |
| Octyldodecanol | 15.5 | 15.5 | — | 14.5 | 10.0 |
| Ceteareth-20 | — | — | 0.5 | — | 0.5 |
| Unilin 425 | 0.5 | 0.5 | 0.5 | 0.5 | 0.5 |
| Al/Zr trichlorohydrex gly. | 25.0 | 25.0 | 25.0 | 24.0 | 25.0 |
| Disodium EDTA | 0.2 | 0.2 | 0.2 | 0.2 | 0.2 |
| Perfume | 1.0 | 1.0 | 1.0 | 2.0 | 1.0 |
| Unithox 450 | 1.25 | 1.25 | — | 1.25 | — |
| Unithox 480 | 1.25 | 1.25 | — | 1.25 | — |
| Isoparaffin (Isopar M) | — | — | 26.0 | — | 10.0 |

EXAMPLES 24–26

The compositions described in Table 5 are deodorant stick compositions. Each of these exemplified compositions can be prepared by methods well known in the art for preparing such product forms, examples of such methods including those described in U.S. Pat. No. 5,605,681 (Trandai et al.) and U.S. Pat. No. 5,585,092 (Trandai et al.), which descriptions are incorporated herein by reference.

TABLE 5

Gel Deodorant Sticks

| Ingredient | Example 24 | Example 25 | Example 26 |
|---|---|---|---|
| Cyclohexasiloxane | 14.7 | 25.0 | 14.7 |
| Permethyl 101A | — | 40.0 | — |
| Isopar M | 41.0 | — | 41.0 |
| Sodium stearate | — | — | 5.5 |
| Octylmethoxyl cinnamate | — | 25.0 | — |
| Butyl stearate | 30.0 | — | 30 |
| Propylene glycol | 0.5 | — | 0.5 |
| Triclosan | 0.3 | — | 0.3 |
| 12-hydroxy stearic acid | 10 | 8.0 | 10.0 |
| Sodium hydroxide | 0.50 | — | — |
| Perfume | 3.0 | 2.0 | 3.0 |

The compositions as described in Tables 1–5 (Examples 1–26) are applied topically to the axilla once or twice daily in an amount sufficient to provide the desired antiperspirant and/or deodorant efficacy, and are applied topically in accordance with the methods described herein. The applied compositions have a dry skin feel during and after application, have improved product stability, low residue performance and cosmetics.

What is claimed is:

1. Antiperspirant compositions comprising:
   a) from about 30% to about 99.8% by weight of cyclohexasiloxane,
   b) from about 0.1% to about 50% by weight of an antiperspirant active,
   c) from about 0.1% to about 50% by weight of a suspending agent, and
   d) from about 1% to about 35% by weight of a nonvolatile polydimethylsiloxane fluid,
   wherein the compositions are substantially free of cyclotetrasiloxane.

2. An antiperspirant composition according to claim 1 wherein the composition contains zero percent by weight of cyclotetrasiloxane.

3. An antiperspirant composition according to claim 1 wherein the composition comprises from about 40% to about 70% by weight of the cyclohexasiloxane.

4. An antiperspirant composition according to claim 1 wherein the composition further comprises from about 1% to about 35% by weight of a suspending agent and from about 1% to about 65% by weight of a carrier liquid other than the cyclohexasiloxane.

5. An antiperspirant composition according to claim 1 wherein the composition contains a volatile silicone material and wherein the volatile silicone material contains from about 45% to 100% cyclohexasiloxane by weight of the volatile silicone material.

6. An antiperspirant composition according to claim 5 wherein the antiperspirant active is selected from the group consisting of aluminum salts, zirconium salts and combinations thereof.

7. Anhydrous antiperspirant compositions comprising
a) from about 20% to about 99.8% % by weight of a cyclohexasiloxane,
b) from about 0.1% to about 50% by weight of an antiperspirant active,
c) from about 0.1% to about 50% by weight of a suspending agent, and
d) from about 1% to about 35% by weight of a nonvolatile polydimethylsiloxane fluid,
wherein the volatile silicone material is substantially free of cylclotetrasiloxane and water.

8. An antiperspirant composition according to claim 7 wherein the composition contains zero percent by weight of cyclotetrasiloxane.

9. An antiperspirant composition according to claim 7 wherein the composition comprises from about 30% to about 70% by weight of the cyclohexasiloxane.

10. An antiperspirant composition according to claim 7 wherein the composition further comprises from about 1% to about 35% by weight of a suspending agent and from about 1% to about 65% by weight of a carrier liquid other than the cyclohexasiloxane.

11. An antiperspirant composition according to claim 7 wherein the composition contains a volatile silicone material and wherein the volatile silicone material contains from about 45% to 100% cyclohexasiloxane by weight of the volatile silicone material.

12. An antiperspirant composition according to claim 7 wherein the antiperspirant active is selected from the group consisting of aluminum salts, zirconium salts and combinations thereof.

13. Aqueous antiperspirant emulsion compositions comprising
a) from about 5% to about 50% by weight of a cyclohexasiloxane,
b) from about 0.1% to about 35% by weight of solubilized antiperspirant active,
c) from about 0.1% to about 50% by weight of a suspending agent,
d) from about 1% wherein the 70% by weight of water, and
e) from about 1% to about 35% by weight of a nonvolatile polydimethylsiloxane fluid,
wherein the composition is in the form of an aqueous emulsion that is substantially free of cyclotetrasiloxane.

14. An antiperspirant composition according to claim 13 wherein the composition contains zero percent by weight of cyclotetrasiloxane.

15. An antiperspirant composition according to claim 13 wherein the composition comprises from about 10% to about 40% by weight of the cyclohexasiloxane.

16. An antiperspirant composition according to claim 13 wherein the composition further comprises from about 1% to about 35% by weight of a suspending agent and from about 1% to about 65% by weight of a carrier liquid other than the cyclohexasiloxane.

17. An antiperspirant composition according to claim 13 wherein the composition contains a volatile silicone material and wherein the volatile silicone material contains from about 45% to 100% cyclohexasiloxane by weight of the volatile silicone material.

18. An antiperspirant composition according to claim 17 wherein the antiperspirant active is selected from the group consisting of aluminum salts, zirconium salts and combinations thereof.

19. Antiperspirant composition comprising
a) from about 1% to about 99% by weight of cyclohexasiloxane,
b) from about 0.1% to about 50% by weight of an antiperspirant active selected from the group consisting of zirconium salts, aluminum salts, and combinations thereof, and
c) from about 0.1% to about 50% by weight of a gellant selected from the group consisting of 12-hydroxysteric acid, 12-hydroxystearic acid esters, 12-hydroxystearic acid amides, n-acyl amino acid ainides, n-acyl amino acid esters, triglyceride gellants, sucrose ester fatty acids, and combinations thereof.

20. Solid or semi-solid deodorant compositions comprising
a) from about 5% to about 99% by weight of cyclohexasiloxane,
b) from about 0.1% to about 50% by weight of deodorant active, and
c) from about 0.1% to about 50% by weight of a suspending agent,
wherein the compositions are substantially free of nitrogen-containing polymers and cyclotctrasiloxane, and wherein the compositions are not in liquid form.

21. A deodorant composition according to claim 2 wherein the composition is substantially free of added water.

22. A deodorant composition according to claim 20 wherein the composition comprises a volatile silicone component, wherein the cyclohexasiloxane represents from about 45% to 100% by weight of the volatile silicone component.

23. A deodorant composition according to claim 20 wherein the composition comprises from about 5% to about 50% by weight of cyclohexasiloxane.

24. A deodorant composition according to claim 22 wherein the composition further comprises from about 1% to about 65% by weight of a carrier liquid other than the cyclohexasiloxane and from about 1% to about 35% by weight of a gellant.

25. A deodorant composition according to claim 24 wherein the gellant is a metal salt of a C12 to C40 fatty acid.

26. A deodorant composition according to claim 25 wherein the gellant is sodium stearate.

27. A deodorant composition according to claim 20 wherein the deodorant active is selected from the group consisting of antimicrobial agents, malodor-absorbing materials, fragrance, deodorant perfumes, and combinations thereof.

28. A deodorant composition according to claim 20 wherein the composition comprise from about 0.01% to about 1% by weight of a deodorant active selected from the group consisting of triclosan, triclocarban and combinations thereof.

29. A method for treating and preventing perspiration in humans, which method comprises the topical application to the axillary area of an effective amount of the antiperspirant and deodorant composition of claim 1.

30. A method for treating and preventing perspiration in humans, which method comprises the topical application to the axillary area of an effective amount of the antiperspirant and deodorant composition of claim 7.

31. A method for treating and preventing perspiration in humans, which method comprises the topical application to the axillary area of an effective amount of the antiperspirant and deodorant composition of claim 13.

32. A method for treating and preventing perspiration in humans, which method comprises the topical application to the axillary area of an effective amount of the antiperspirant and deodorant composition of claim 19.

33. A method for treating and preventing perspiration malodor in humans, which method comprises the topical application to the axillary area of an effective amount of the deodorant composition of claim 20.

* * * * *

UNITED STATES PATENT AND TRADEMARK OFFICE
CERTIFICATE OF CORRECTION

PATENT NO.    : 6,183,730 B1
DATED         : February 6, 2001
INVENTOR(S)   : G.J. Guskey et al.

Page 1 of 1

It is certified that error appears in the above-identified patent and that said Letters Patent is hereby corrected as shown below:

<u>Column 16,</u>
Line 4, "ainides" should read -- amides --.
Line 16, "cyclotctrasiloxane" should read -- cyclotetrasiloxane --.

Signed and Sealed this

Twenty-second Day of March, 2005

JON W. DUDAS
*Director of the United States Patent and Trademark Office*